United States Patent
Bosch Lladó et al.

(10) Patent No.: US 6,521,787 B1
(45) Date of Patent: Feb. 18, 2003

(54) NON-HYDRATED GABAPENTINE POLYMORPH, PRODUCTION PROCESS AND UTILIZATION FOR PRODUCING PHARMACEUTICAL GRADE GABAPENTINE

(75) Inventors: Jordi Bosch Lladó, Gerona (ES); Rafael García Cruz, Sant Celoni (ES); Elias Molins Grau, Sant Feliu de Llobregat (ES); Maria del Carmen Onrubia Miguel, Barcelona (ES)

(73) Assignee: Medichem, S.A., Barcelona (ES)

( * ) Notice: Subject to any disclaimer, the term of this patent is extended or adjusted under 35 U.S.C. 154(b) by 0 days.

(21) Appl. No.: 09/700,939
(22) PCT Filed: May 10, 1999
(86) PCT No.: PCT/ES99/00127
§ 371 (c)(1), (2), (4) Date: Nov. 21, 2000
(87) PCT Pub. No.: WO99/61408
PCT Pub. Date: Dec. 2, 1999

(30) Foreign Application Priority Data

May 25, 1998 (ES) .............................................. 9801078

(51) Int. Cl.[7] ........................ C07C 229/00; A01N 43/36
(52) U.S. Cl. ........................ 562/507; 514/408; 548/561
(58) Field of Search ........................ 562/507; 548/408; 514/561

(56) References Cited

U.S. PATENT DOCUMENTS

| 4,024,175 | A | * | 5/1977 | Satzinger et al. ............ 260/468 |
| 4,087,544 | A | * | 5/1978 | Satzinger et al. ............ 260/468 |
| 4,960,931 | A | * | 10/1990 | Butler et al. |
| 5,068,413 | A | * | 11/1991 | Steiner et al. |

FOREIGN PATENT DOCUMENTS

| EP | 0 340 677 | 2/1994 |
| ES | 443 723 | 12/1974 |

* cited by examiner

*Primary Examiner*—Alan L. Rotman
*Assistant Examiner*—Héctor M Reyes
(74) *Attorney, Agent, or Firm*—Scully, Scott, Murphy & Presser

(57) ABSTRACT

The non-hydrated gabapentin polymorph is prepared by drying an aqueous solution of gabapentin by spray drying or turbo-drying and it is used for the preparation of pharmaceutical grade gabapentin by subjecting the polymorph to crystallisation from solvents.

14 Claims, 2 Drawing Sheets

NON-HYDRATED GABAPENTINE POLYMORPH, PRODUCTION PROCESS AND UTILIZATION FOR PRODUCING PHARMACEUTICAL GRADE GABAPENTINE

FIELD OF THE INVENTION

The present invention relates to a crystalline polymorph of non-hydrated gabapentin and to the utility thereof as a starting product for the preparation of pharmaceutical grade gabapentin. Likewise, the invention relates to processes for the preparation of the new crystalline polymorph and for the preparation of pharmaceutical grade gabapentin.

PRIOR ART REFERENCE

Gabapentin is a synthetic amino acid related to γ-aminobutyric acid (GABA) responding to the chemical name of 1-(aminomethyl) cyclohexane acetic acid (The Merck Index, Ed. XII) and the following formula

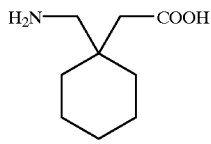

The said compound has a therapeutical activity for convulsive type cerebral disorders, such as epilepsy, hypokinesia, including fainting, and other brain trauma and, in general, it is deemed to produce an improvement of the cerebral functions.

Gabapentin and several processes for the preparation thereof are described in Spanish patent ES-A-443 723, corresponding to U.S. Pat. No. 4,024,175, Example 1 of which describes the preparation of the free amino acid from the hydrochloride thereof, by treatment of an aqueous solution thereof with a basic ion exchanger, evaporation of the solvent and subsequent crystallisation from ethanol/ether.

The thus obtained product corresponds to a non-hydrated crystalline form coinciding with the one shown by the commercial pharmaceutical Neurontin® which is the pharmaceutical standard for gabapentin.

On the other hand, EP-B-0 340 677 and the Spanish part thereof, ES-T3-2 061 774, disclose a new hydrated form of gabapentin characterised by its X-ray diffraction data and the process for the preparation thereof, as well as a process for preparing the non-hydrated crystalline form requiring the prior preparation of the said hydrated form. Said process consists of the following successive steps:

a) passing an aqueous gabapentin hydrochloride solution through a basic ion exchange column.
b) concentrating the eluate to form a suspension.
c) cooling and adding alcohol to the above suspension.
d) cooling and centrifuging the thus prepared suspension.
e) drying the product obtained, which is the hydrated form of gabapentin.
f) dissolving the above pure hydrated form in methanol.
g) diluting and cooling the thus prepared solution until a suspension is obtained.
h) centrifuging the suspension and drying the product, which is the non-hydrated form of gabapentin.

The above described process is obviously complicated from the industrial point of view, since it requires several steps and the isolation of an intermediate in pure form, the hydrated form, prior to a final crystallisation. All of this leads to an excessive occupation of the industrial plant and losses in the yield of the desired product.

There is, therefore, a need to develop alternative processes for the preparation of non-hydrated pharmaceutical grade gabapentin allowing the industrial preparation of the product to be simplified, with a consequent reduction of the production costs.

SUMMARY OF THE INVENTION

It is an object of the present invention to provide an non-hydrated gabapentin polymorph allowing pharmaceutical grade gabapentin to be prepared in an industrially improved way over the prior art.

It is also an object of the invention to provide a process for the preparation of said polymorph and a process for the preparation of pharmaceutical grade gabapentin from said polymorph.

DETAILED DESCRIPTION

Figure 1:
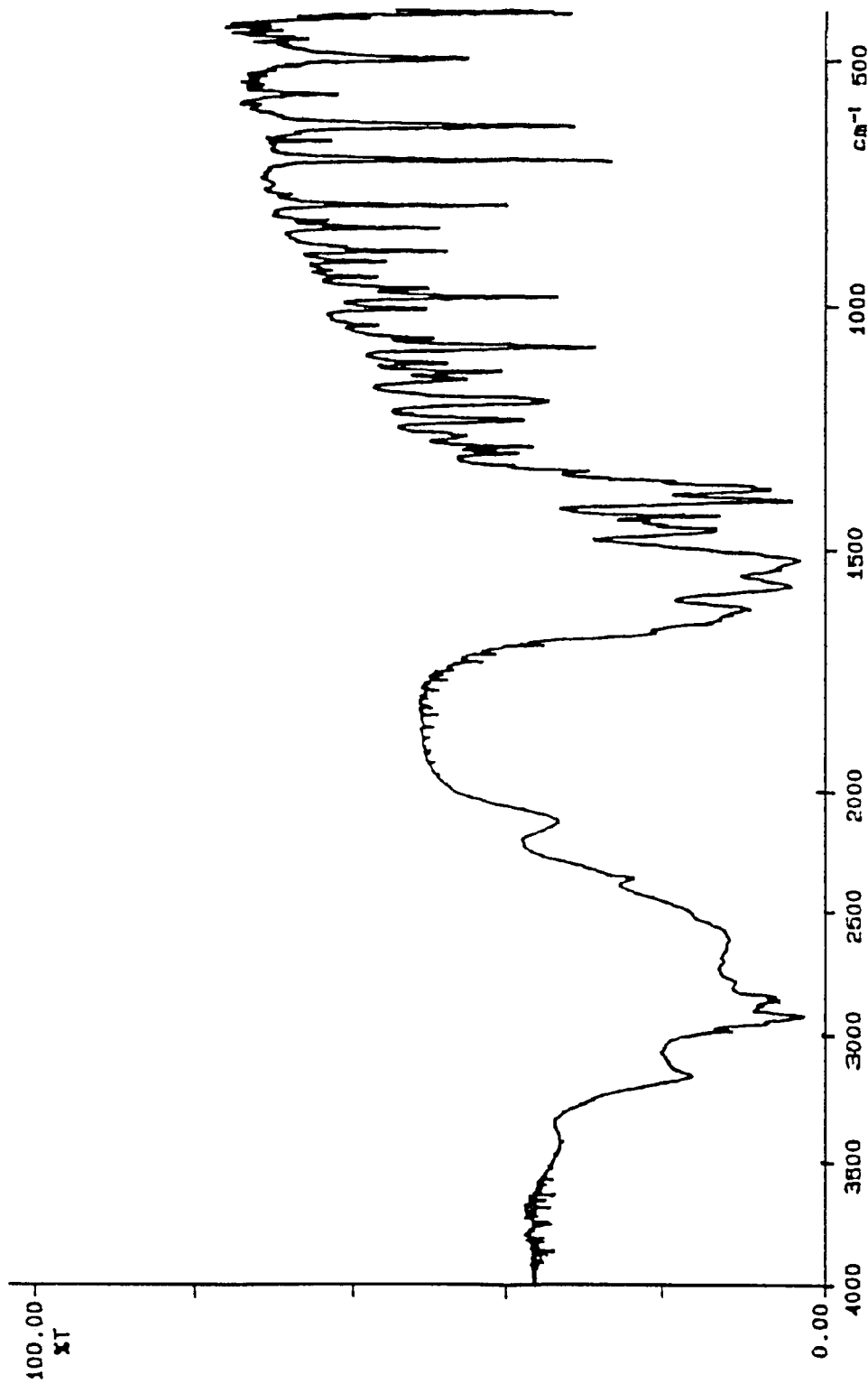
FIG. 1 is an IR spectrum of the non-hydrated gabapentin polymorph of the invention, using KBr tablet.
Figure 2:
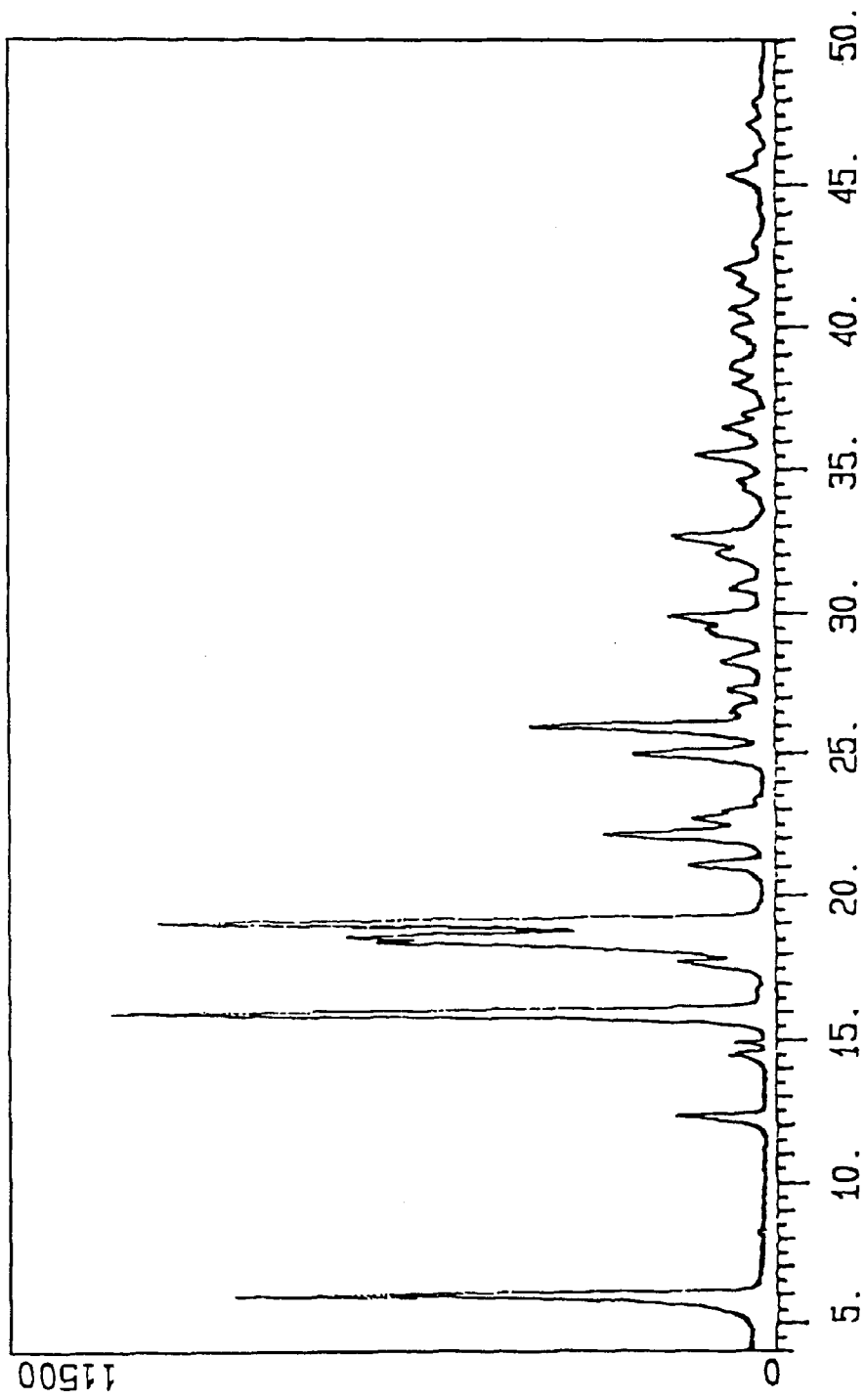
FIG. 2 is an X-ray diffraction diagram of said polymorph, with a diffraction angle coverage ranging from 4° to 50° in 0.02° steps.

The present inventors have discovered that by drying an aqueous solution of gabapentin using spray-drying or turbo-drying techniques, a new non-hydrated gabapentin polymorph is obtained and which has been named Form II by the inventors. The IR spectrum, on KBr tablet, is shown in FIG. 1 and the X-ray diffraction diagram with a diffraction angle coverage ranging from 4° to 50° in 0.02° steps is shown in FIG. 2.

Table 1 gives numerically the spacing "d" in Å and the relative intensity I (%) of the said X-ray diffraction diagram, for the peaks having a relative intensity equal or superior to 5.

TABLE 1

X-ray diffraction of the gabapentin Form II polymorph

| d | I (%) |
|---|---|
| 14.67 | 100 |
| 7.20 | 13 |
| 6.14 | 5 |
| 5.55 | 90 |
| 5.02 | 11 |
| 4.90 | 20 |
| 4.76 | 58 |
| 4.65 | 81 |
| 4.22 | 10 |
| 4.02 | 21 |
| 3.93 | 10 |
| 3.56 | 17 |
| 3.43 | 33 |
| 3.27 | 5 |
| 3.16 | 5 |
| 3.00 | 12 |
| 2.79 | 6 |
| 2.74 | 11 |

TABLE 1-continued

X-ray diffraction of the gabapentin Form II polymorph

| d | I (%) |
|---|---|
| 2.53 | 8 |
| 2.46 | 5 | d = spacing in Å;
I (%) = relative intensity

In turn, for comparative purposes, the X-ray diffraction diagram corresponding to the pharmaceutical grade gabapentin standard, which the present inventors have named Form I, obtained under the same conditions, gives the results listed in Table 2.

TABLE 2

X-ray diffraction of the gabapentin Form I polymorph

| d | I (%) |
|---|---|
| 11.13 | 100 |
| 5.89 | 30 |
| 5.22 | 29 |
| 4.35 | 18 |
| 4.17 | 6 |
| 3.85 | 6 |
| 3.77 | 18 |
| 3.46 | 12 |
| 3.30 | 13 |
| 3.16 | 6 | d = spacing in Å;
I (%) = relative intensity

Having regard to the IR spectrum, the most significant bands of the new Form II polymorph, in comparison with the Form I polymorph, may be said to be those occurring at 1576, 1522, 985 and 637 $cm^{-1}$.

The present inventors have also found that when the new Form II polymorph is crystallised out of conventional solvents, there is surprisingly obtained pharmaceutical grade non-hydrated gabapentin, i.e. the Form I polymorph is obtained with a high degree of purity and a high yield.

Thus, pharmaceutical grade Form I gabapentin may be obtained on an industrial scale without it being necessary previously to prepare a pure hydrated form thereof, by a process, also an object of the invention, consisting essentially of crystallising the non-hydrated gabapentin Form II polymorph in a conventional solvent or mixture of solvents.

The aqueous gabapentin starting solution for preparing the Form II polymorph may be prepared by the method described in any of the aforementioned documents ES-A-443 723 and EP-B-0 340 677. The concentration of the solution may range from 2% to 11% by weight, although concentrations ranging from 5% to 7% by weight are to be preferred.

The gabapentin solution is not dried by conventional evaporation of the solvent, but by spray-drying or turbo-drying techniques, in equipment well known to the man of the art.

The air inlet temperature to the spray drier or turbo-drier may range from 100° C. to 200° C., preferably from 105° C. to 110° C. and the exit temperature may range from 60° C. to 120° C., preferably from 75° C. to 85° C.

As previously mentioned, the Form II polymorph is converted to the Form I polymorph by conventional crystallisation methods by using also conventional solvents, although the short chain alcohols and/or mixtures of these alcohols with water are preferred. The presence of small amounts of water in the crystallisation process allows smaller volumes to be used, with the consequent saving, and provides pharmaceutical grade gabapentin (Form I) of a high degree of purity. Methanol, ethanol and isopropanol may be cited among the most preferred alcohols.

The following Examples are provided for the purpose of giving the man of the art a sufficiently clear and complete explanation of the present invention, but must not be deemed to be limitations on the essential aspects of the object of the invention, such as those indicated in the foregoing paragraphs hereof.

EXAMPLES

Example 1

Following the method described in Example 1 of EP-B-0 340 677, 1.5 L of an aqueous solution of gabapentin containing 73.8 g/L was obtained. Said solution was dried using a type A/S spray-drier, supplied by NIRO, under the following conditions: flowrate 5.80 L/h, air input temperature 106–109° C. and exit temperature 77–78° C. 101.8 g of non-hydrated gabapentin, Form II, were obtained in the form of a white powder having a melting point of 164–5° C., a specific gravity of 0.502 g/mL and a chromatographic purity (HPLC) of 99.3%. The gabapentin obtained showed a solid state (KBr) infra red spectrum and an X-ray diffraction spectrum in powder conforming to those given in FIGS. 1 and 2 and in Table 1.

An aliquot (10.2 g) of the Form II gabapentin obtained was dissolved in a mixture of 89 mL of methanol and 1 mL of water at a temperature of 60°–65° C. The resulting solution was cooled to 20° C. and the appearance of a white precipitate was observed. 90 mL of isopropanol were added, with subsequent cooling to 0°–5° C. and stirring was continued at that temperature for 4 hours. The precipitate was filtered and dried, to give 8.4 g (82%) of Form I gabapentin, with a chromatographic purity (HPLC) of 99.7%. The X-ray diffraction data conform to those given in Table 2.

Example 2

When operating in the same way as described in example 1, but with the following variations: gabapentin solution concentration 6% by weight, spray drier flowrate 9 L/h, air input temperature 170°–180° C. and air exit temperature 110°–115° C., non-hydrated Form II gabapentin was prepared, with a chromatographic purity (HPLC) of 92.6%, with the solid state (KBr) infra red ray spectrum and powder X-ray diffraction spectrum being in agreement with those given in FIGS. 1 and 2 and Table 1.

Example 3

900 mL of a 6% by weight aqueous solution of gabapentin were evaporated in a Rinajet® turbo-drier, under the following conditions: flowrate 0.45 L/h, air input temperature 120 °–130° C. and air exit temperature 80°–85° C. Non-hydrated Form II gabapentin was prepared, with a chromatographic purity (HPLC) of 94.6%, with the solid state (KBr) infra red ray spectrum and powder X-ray diffraction spectrum thereof being in agreement with those given in FIGS. 1 and 2 and Table 1.

Example 4

Following the method described in Example 1 of EP-B-0 340 677, 1.5 L of an aqueous solution of gabapentin containing 73.8 g/L was obtained. Said solution was dried using a type A/S spray-drier, supplied by NIRO, under the following conditions: flowrate 7.33 L/h, air input temperature 140–143° C. and exit temperature 92–95° C. The product obtained was gabapentin Form II, the infra red spectrum and X-ray diffraction spectrum thereof being in agreement with those given in FIGS. 1 and 2 and in Table 1.

Example 5

10.2 g of the Form II gabapentin obtained in Example 4 were dissolved in a mixture of 94 mL of methanol and 1 mL of water at a temperature of 64° C. The resulting solution was cooled to 20 °–25° C. and the appearance of a white precipitate was observed. 90 mL of isopropanol were added, with subsequent cooling to 0°–25° C. and stirring was continued at that temperature for 4 hours. The precipitate was filtered and dried, to give 7.7 g (75%) of Form I gabapentin, with a chromatographic purity (HPLC) of 99.7%. The X-ray diffraction data conform to those given in Table 2.

Example 6

10.1 g of the Form II gabapentin obtained in Example 4 were dissolved in a mixture of 94 mL of ethanol and 1 mL of water at a temperature of 79° C. The resulting solution was cooled to 0°–5° C. and stirring was continued at that temperature for 3 hours 15 minutes. The precipitate was filtered and dried, to give 8.3 g (82%) of Form I gabapentin, with a chromatographic purity (HPLC) of 99.3%. The X-ray diffraction data conform to those given in Table 2.

What is claimed is:

1. Non-hydrated gabapentin polymorph having substantially the following X-ray diffraction data:

| d | I (%) |
|---|---|
| 14.67 | 100 |
| 7.20 | 13 |
| 6.14 | 5 |
| 5.55 | 90 |
| 5.02 | 11 |
| 4.90 | 20 |
| 4.76 | 58 |
| 4.65 | 81 |
| 4.22 | 10 |
| 4.02 | 21 |
| 3.93 | 10 |
| 3.56 | 17 |
| 3.43 | 33 |
| 3.27 | 5 |
| 3.16 | 5 |
| 3.00 | 12 |
| 2.79 | 6 |
| 2.74 | 11 |
| 2.53 | 8 |
| 2.46 | 5 | d = spacing in Å;
I (%) = relative intensity.

2. A process for the preparation of the non-hydrated gabapentin polymorph according to claim 1, wherein an aqueous solution of gabapentin is subjected to spray-drying or turbo drying.

3. The process according to claim 2, wherein said aqueous gabapentin solution has a concentration of from 2% to 11% by weight.

4. The process according to claim 3, wherein said aqueous gabapentin solution has a concentration of from 5% to 7% by weight.

5. The process according to one of claims 2 to 4, wherein the air inlet temperature to the spray drier or turbo drier ranges from 100° C. to 200° C. and the air exit temperature ranges from 60° C. to 120° C.

6. The process according to claim 5, wherein the air inlet temperature to the spray drier or turbo drier ranges from 105° C. to 110° C. and the air exit temperature ranges from 75° C. to 85° C.

7. A process for the preparation of a Form I polymorph of gabapentin having substantially the following X-ray diffraction data:

| D | I (%) |
|---|---|
| 11.13 | 100 |
| 5.89 | 30 |
| 5.22 | 29 |
| 4.35 | 18 |
| 4.17 | 6 |
| 3.85 | 6 |
| 3.77 | 18 |
| 3.46 | 12 |
| 3.30 | 13 |
| 3.16 | 6 | d = spacing in Å;
I (%) = relative intensity wherein a non-hydrated polymorph having substantially the following X-ray diffraction data:

| D | I (%) |
|---|---|
| 14.67 | 100 |
| 7.20 | 13 |
| 6.14 | 5 |
| 5.55 | 90 |
| 5.02 | 11 |
| 4.90 | 20 |
| 4.76 | 58 |
| 4.65 | 81 |
| 4.22 | 10 |
| 4.02 | 21 |
| 3.93 | 10 |
| 3.56 | 17 |
| 3.43 | 33 |
| 3.27 | 5 |
| 3.16 | 5 |
| 3.00 | 12 |
| 2.79 | 6 |
| 2.74 | 11 |
| 2.53 | 8 |
| 2.46 | 5 | d = spacing in Å;
I (%) = relative intensity is crystallized from a solvent or mixture of solvents.

8. The process according to claim 7, wherein said solvents used are short chain alcohols and water or mixtures thereof.

9. The process according to claim 8 wherein said solvents are selected from the group formed by methanol, ethanol, isopropanol and water.

10. The process as in claim 8 or 7, wherein the preparation of the non-hydrated gabapentin polymorph having substantially the following X-ray diffraction data:

| D | I (%) |
|---|---|
| 14.67 | 100 |
| 7.20 | 13 |

-continued

| D | I (%) |
|---|---|
| 6.14 | 5 |
| 5.55 | 90 |
| 5.02 | 11 |
| 4.90 | 20 |
| 4.76 | 58 |
| 4.65 | 81 |
| 4.22 | 10 |
| 4.02 | 21 |
| 3.93 | 10 |
| 3.56 | 17 |
| 3.43 | 33 |
| 3.27 | 5 |
| 3.16 | 5 |
| 3.00 | 12 |
| 2.79 | 6 |
| 2.74 | 11 |
| 2.53 | 8 |
| 2.46 | 5 | d = spacing in Å;
I (%) = relative intensity further comprises a step wherein an aqueous solution of gabapentin is subjected to spray-drying or turbo drying.

11. The process according to claim 10, wherein said aqueous gabapentin solution has a concentration of from 2% to 11% by weight.

12. The process according to claim 10 wherein said aqueous gabapentin solution has a concentration of from 5% to 7% by weight.

13. The process according to claim 10, wherein the air inlet temperature to the spray drier or turbo drier ranges from 100° C. to 200° C. and the air exit temperature ranges from 60° C. to 120° C.

14. The process according to claim 10, wherein the air inlet temperature to the spray drier or turbo drier ranges from 105° C. to 110° C. and the air exit temperature ranges from 75° C. to 85° C.

* * * * *